United States Patent [19]
Yoshida et al.

[11] Patent Number: 5,674,896
[45] Date of Patent: Oct. 7, 1997

[54] APPETITE SUPPRESSING AGENT AND USE THEREOF

[75] Inventors: Ryuji Yoshida; Hirokazu Maeda, both of Kitasoma-gun; Naomi Higuchi, Izumisano; Takashi Yamamoto; Toshiaki Aoyama, both of Sennan-gun; Miyuki Shibata, Osaka, all of Japan

[73] Assignee: Fuji Oil Company, Limited, Osaka, Japan

[21] Appl. No.: 953,779

[22] Filed: Sep. 30, 1992

Related U.S. Application Data

[63] Continuation of Ser. No. 643,930, Jan. 22, 1991, abandoned.

[30] Foreign Application Priority Data

Jan. 22, 1990 [JP] Japan ..................... 2-12996

[51] Int. Cl.$^6$ ................ A61K 31/22; A61K 31/23
[52] U.S. Cl. ........................... 514/549; 514/552
[58] Field of Search ................... 514/533, 549, 514/909, 910, 552

[56] References Cited

U.S. PATENT DOCUMENTS 4,701,468   10/1987   Mendy ..................... 514/547

FOREIGN PATENT DOCUMENTS 767742    3/1976   France .
1516489   7/1978   United Kingdom .

*Primary Examiner*—Raymond Henley, III
*Attorney, Agent, or Firm*—Wenderoth, Lind & Ponack

[57] ABSTRACT

An agent for depressing ingestion of food as well as food and feed containing such an agent are disclosed. The agent may be one or plurality of triglycerides containing fatty acid residues having not more than 10 carbon atoms at 1,3-positions thereof and stearic acid residue at 2-position thereof. The agent may also be a fat or oil containing the triglycerides.

10 Claims, 1 Drawing Sheet

APPETITE SUPPRESSING AGENT AND USE THEREOF

This application is a continuation of now abandoned application Ser. No. 07/643,930, filed Jan. 22, 1991, now abandoned.

FIELD OF THE INVENTION

The present invention relates to an appetite suppressing agent and the use thereof. More particularly, it relates to an agent for suppressing appetites and the use thereof as food and feed for controlling fatness, and the like.

BACKGROUND OF THE INVENTION

There are people who want to control overeating so as to inhibit fatness. Also, there are people who have become fat or obese and have been forced to improve their diet.

Further, the mode of life of people influences the eating habits of their pets and, in their pets, there is also the problem of inhibiting fatness due to overeating.

However, alimentotherapy (dietotherapy) by controlling ingestion of fats and oils and the like often forces people to have unpalatable or, at least, non-attractive diets, and it is not necessarily easy to continue such an alimentotherapy. Further, although various low calorie foods, for example, fatty acid sucrose polyesters have been developed as a fat substitute having low absorption property in the body, but such a substitute itself is not absorbed in the body and excreted in a liquid state and, therefore, there are disadvantages. For example, when the substitute is ingested alone, diarrhea is caused.

Further, although some anorectics have been reported, they require intravenous injection or, sometimes, cause pain even in a small dosage due to their violent effects.

In order to provide a material which is in the form of a fat or oil, but is easily cooked and ingested and has a low absorption property in the body, the present inventors intensively studied and already filed patent applications [JP-A 64-85040 (WPI Acc No: 89-140743); and JP-A 2-158695 (WPI Acc No: 90-229194)]. Further, EP-A 0 322 027 discloses reduced calorie fats made from triglycerides containing medium and long chain fatty acids. This EP-A 0 322 027 describes the finding that "triglycerides fats made with long chain or very long chain saturated fatty acids are reduced in calories because the fatty acids are only poorly absorbed and metabolized by the body" as well as the finding that "the absorption of long chain fatty acids is generally reduced in the end positions (1 or 3 position)".

Now, it has been found that, among these fats and oils which are only poorly absorbed by the body, there are some specific glycerides which can suppress appetites. Further, it has been found that such glycerides should contain a stearic acid residue at 2-position thereof and, if a stearic acid residue is bound to the end positions (1 or 3 position), such triglycerides do not suppress appetites. Furthermore, it has been found that, when a fatty acid residue bound to 2-position is a long chain fatty acid residue such as behenic acid residue, no depression effect is obtained.

OBJECTS OF THE INVENTION

One object of the present invention is to provide an agent in the form of a fat or oil which suppresses appetites and can substitute for other fats or oils without any different nature, and which can be ingested without any pain.

Another object of the present invention is to provide food containing as an essential ingredient the above agent of the present invention.

Still another object of the present invention is to provided feed containing as an essential ingredient the above agent of the present invention.

These objects as well as other objects and advantages of the present invention will become apparent to those skilled in the art from the following description with reference to the accompanying drawings.

Figure 1:
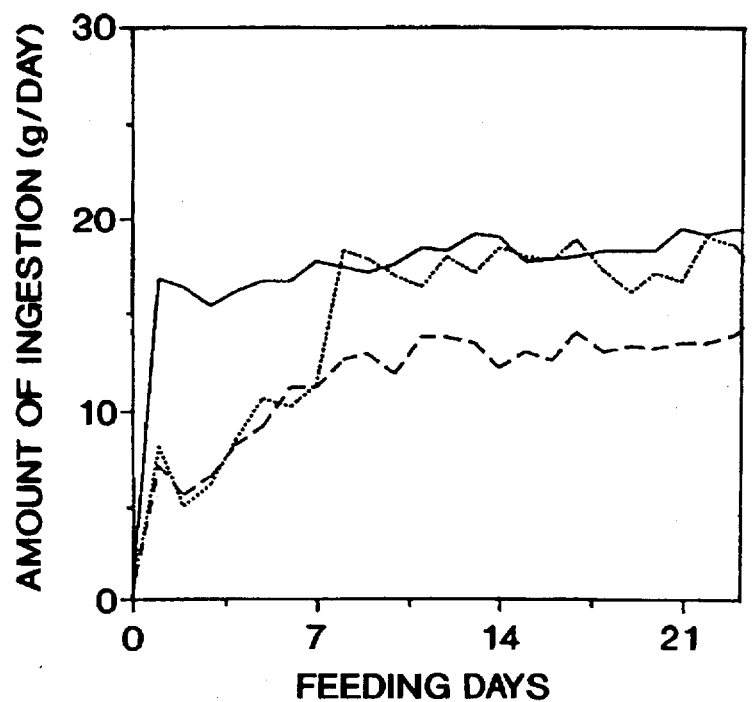
FIG. 1 is a graph showing the relation between the amount of feed and the number of feeding days obtained in Experiment 2 hereinafter.

In these graphs, the solid line represents the use of corn oil in the feed; the dotted line represents the use of the agent of the present invention for one week and then corn oil in the feed; and the broken line represents the use of the agent of the present invention in the feed.

SUMMARY OF THE INVENTION

According to the present invention, there is provided an agent for suppressing appetites which comprises one or plurality of triglycerides containing fatty acid residues having not more than 10 carbon atoms at 1,3-positions thereof and stearic acid residue at the 2-position thereof. The present invention also provides food comprising an appetite suppressing effective amount of one or plurality of triglycerides containing fatty acid residues having not more than 10 carbon atoms at the 1,3-positions thereof and a stearic acid residue at 2-position thereof. The present invention further provides feed comprising an appetite suppressing effective amount of one or plurality of triglycerides containing fatty acid residues having not more than 10 carbon atoms at the 1,3-positions thereof and a stearic acid residue at the 2-position thereof.

DETAILED DESCRIPTION OF THE INVENTION

The triglycerides in the present invention should have specific fatty acids residues at specific positions. For example, even if triglycerides contain two fatty acid residue having not more than 10 carbon atoms and one stearic acid residue, no desired effect can be obtained, when stearic acid is bound at the 1- or 3-position. Further, even if triglyceride contain fatty acid residues having not more than 10 carbon atoms at the 1,3-positions thereof, no desired effect can be obtained, when the fatty acid residue at the 2-position is a long chain fatty acid residue such as behenic acid residue, or parmitic acid residue which has 16 carbon atoms.

The fatty acid residues bound at the 1,3-positions are, preferably, straight chain saturated fatty acid residues having 2 to 8 carbon atoms, more preferably, 6 to 8 carbon atoms.

The above specific triglycerides do not have any taste and smell and the triglycerides per se can be ingested without any difficulty. Further, their melting point is lower than the body temperature. Therefore, there are advantages that the triglycerides can be easily substituted for fats and oils in food and feed, and diarrhea, which is often caused by using conventional fat substitutes, is not caused.

The agent of the present invention may be at least one such a specific triglyceride itself or may be a fat or oil containing at least one such a specific triglyceride. There is no necessity that the triglycerides of the present invention be pure substances. However, when the amount of the triglycerides in entire triglycerides or fats and oils is higher, appetite suppression is increased. Usually, when the amount is less than 35% by weight based on the total weight of triglycerides or fats and oils, ingestion of food is scarcely diminished. Therefore, when stearic acid residue is randomly bound at 1-, 2- and 3-positions, the desired effect is scarcely obtained. Preferably, the specific triglycerides are contained in an amount of not less than 50% by weight.

The triglycerides or the fat or oil containing them can be produced by any known process. For example, they can be obtained by introducing fatty acid residues having not more than 10 carbon atoms at the 1,3-positions of triglycerides containing a fatty acid residue having 18 carbon atoms at the 2-position or a fat or oil which is rich in such triglycerides, if necessary, hydrogenating the fatty acid residue having 18 carbon atoms bound at 2-position before or after the above introduction and further, if necessary, subjecting to fractionation and purification.

The introduction of the above fatty acid residues can be carried out by any known ester interchange process or by a selective ester interchange process. For example, a selective ester interchange can be carried out by using enzymes according to processes disclosed in U.S. Pat. Nos. 4,268,527, 4,416,991, 4,275,081 and 4,275,011; and British Patent No. 2,159,527, herein incorporated by reference.

The agent of the present invention can be used by internally administering it to depress ingestion of food. The mode of administration is not limited to a specific one and the agent may be administered in the form of, for example, tablets and capsules produced by a known method.

However, usually, the agent of the present invention is provided in the form of food or, for pets, feed by substituting the agent for all or a part of the fatty ingredients of the conventional food or feed. That is, the food or feed of the present invention comprises as an essential ingredient an appetite supressing effective amount of one or plurality of the triglycerides. Usually, these food or feed contains the triglycerides in an amount of, at least, 35% by weight, preferably, not less than 50% by weight based on the weight of the fat and oil ingredient of food or feed. When control for overeating is required, the agent of the present invention is administered in the amount of about 0.05 to 10 g/kg body weight per day as a fat or oil. Further, the agent can be administered by alternatively ingesting ordinary food or feed with food or feed containing the agent at suitable intervals. The food may be, for example, oils for frying, shallow pan oil, margarine, shortening, cooking oils, mayonnaise, dressing and the like. Further, they may be oily confectioneries (e.g., cookie, chocolate), dairy products (e.g., cream), fats and oils for medical foodstuffs, imitation meats containing fats and oils as raw materials and the like. The feed may be conventional ones. The food and feed according to the present invention have improved taste and is easily fed in comparison with various conventional diet food using no fats and oils.

The following Examples and Experiments further illustrate the present invention in detail but are not to be construed to limit the scope thereof. In the Examples and Experiments, all "parts" and "percents" are by weight unless otherwise stated.

EXAMPLE 1

Tristearin (60.6 parts) was subjected to ester interchange by using ethyl capronate (39.4 parts) and lipase having 1,3-position selectivity. Ethyl ester of the fatty acids was removed and the reaction mixture was subjected to solvent fractionation with hexane to remove a high melting point fraction to obtain a low melting point fraction (Fat I), yield: 37.6%.

EXAMPLE 2

Sunflower oil containing high oleic acid (43.6 parts) was subjected to ester interchange by using ethyl caprylate (56.4 parts) and lipase having 1,3-position selectivity. Ethyl ester of the fatty acids was removed and the reaction mixture was subjected to fully hydrogenation. Then, the hydrogenated oil was subjected to solvent fractionation with hexane to remove a high melting point fraction to obtain a low melting point fraction (Fat II), yield: 39.0%.

For comparison, according to the same manner as that described in Examples 1 and 2, Fats III to VII were obtained except for using the conditions as shown in Table 1. Regarding Fat VI, a low melting point fraction was obtained by a molecular distillation.

Each yield shown in Table 1 is that of a low melting point fraction.

The fatty acid compositions of the main triglyceride of Fats I to VII are as follows:

Fat I: $C_6$ saturated-$C_{18}$ saturated-$C_6$ saturated;

Fat II: $C_8$ saturated-$C_{18}$ saturated-$C_8$ saturated;

Fat III: $C_6$ saturated-$C_6$ saturated-$C_{18}$ saturated;

Fat IV: $C_6$ saturated-$C_{22}$ saturated-$C_6$ saturated;

Fat V: $C_6$ saturated-$C_{16}$ saturated-$C_6$ saturated;

Fat VI: $C_6$ saturated-$C_{18}$ unsaturated-$C_6$ saturated;

Fat VII: $C_{18}$ unsaturated-$C_{18}$ saturated-$C_{18}$ unsaturated.

TABLE 1

| Fat No. | Raw material | Amounts (parts) | Yield (%) |
| --- | --- | --- | --- |
| III | tricapron | 38.2 | 58.6 |
|  | ethyl stearate | 61.6 |  |
| IV | tribehen | 64.8 | 34.5 |
|  | ethyl capronate | 35.2 |  |
| V | tripalmitin | 50.0 | 45.8 |
|  | ethyl capronate | 50.0 |  |
| VI | high oleic sunflower oil | 60.6 | 30.1 |
|  | ethyl capronate | 39.4 |  |
| VII | tristearin | 33.3 | 49.7 |
|  | ethyl oleate | 66.7 |  |

The fatty acid compositions (molar ratio), triglyceride (TG) compositions (% by weight) and melting points of Fats I to VII are shown in Table 2.

The melting point is a softening point (°C.) determined according to Japan Oil Chemistry Association, "standard test method for the analysis of fats and oils", 2.3.4.3-86. The sample was prepared by solidification with standing at −15° C. for 60 minutes in place of solidification with standing on ice for 15 minutes.

TABLE 2

| Fat No. | I | II | III | IV | V | VI | VII |
| --- | --- | --- | --- | --- | --- | --- | --- |
| Fat composition and melting point | | | | | | | |
| (Fatty acid composition) | | | | | | | |
| $C_4$ | — | 0.2 | 0.3 | — | 0.4 | 0.1 | — |
| $C_6$ | 57.7 | 0.3 | 58.7 | 61.0 | 61.0 | 59.9 | — |

TABLE 2-continued

Fat composition and melting point

| Fat No. | I | II | III | IV | V | VI | VII |
|---|---|---|---|---|---|---|---|
| $C_8$ | — | 59.0 | 1.6 | — | — | — | — |
| $C_{10}$ | — | — | 0.2 | — | — | — | — |
| $C_{14}$ | — | — | — | — | — | 0.1 | — |
| $C_{16}$ | 2.7 | 3.8 | 0.6 | — | 38.6 | 0.5 | 2.9 |
| $C_{18}$ | 39.3 | 36.7 | 38.3 | 0.1 | — | — | 30.8 |
| $C_{18}F_1$ | — | — | — | — | — | 34.6 | 56.2 |
| $C_{18}F_2$ | — | — | — | — | — | 4.8 | 9.3 |
| $C_{20}$ | 0.1 | — | 0.2 | 3.9 | — | — | 0.3 |
| $C_{22}$ | 0.2 | — | — | 34.1 | — | — | — |
| $C_{24}$ | 0.1 | — | — | 0.9 | — | — | — |

(TG composition)

| | | | | | | | |
|---|---|---|---|---|---|---|---|
| $C_{24}$ | — | — | — | — | 0.1 | — | — |
| $C_{26}$ | 3.0 | — | 3.0 | — | 0.1 | — | — |
| $C_{28}$ | 0.1 | — | 1.7 | — | 80.8 | 0.4 | — |
| $C_{30}$ | 74.0 | 0.5 | 72.4 | 3.2 | 2.1 | 85.1 | — |
| $C_{32}$ | — | 0.6 | 3.8 | 4.8 | — | — | — |
| $C_{34}$ | — | 79.2 | 0.6 | 72.5 | 0.2 | — | — |
| $C_{36}$ | — | — | — | 2.0 | 0.1 | — | — |
| $C_{38}$ | — | — | — | — | 11.6 | 0.2 | — |
| $C_{40}$ | 8.7 | 0.1 | 1.7 | — | 0.8 | 1.0 | — |
| $C_{42}$ | 11.0 | 9.5 | 10.9 | — | — | 9.5 | — |
| $C_{44}$ | 0.5 | 6.1 | 1.2 | 0.6 | — | — | — |
| $C_{46}$ | 0.6 | 0.2 | 0.2 | 3.0 | — | — | — |
| $C_{48}$ | 0.9 | 0.4 | 0.4 | 6.2 | 0.2 | — | — |
| $C_{50}$ | — | 0.1 | 1.0 | 6.6 | — | — | 0.3 |
| $C_{52}$ | 0.5 | 0.1 | 1.2 | 1.1 | — | 0.1 | 7.2 |
| $C_{54}$ | 0.7 | 0.3 | 2.0 | — | — | 0.3 | 91.0 |
| $C_{56}$ | — | — | — | — | — | 0.2 | — |
| m.p. | 24.4 | 27.8 | 14.1 | 36.2 | 19.4 | — | 17.1 |

TABLE 3

Composition of feed

| Raw material | Composition (parts by weight) |
|---|---|
| Casein powder (*3) | 20 |
| DL-methionine | 0.3 |
| α-Cornstarch | 15 |
| Sucrose | 35 |
| Fat to be tested | 18 |
| Corn oil (*2) | 2 |
| Cellulose powder | 5 |
| Mineral mix (*1) | 3.5 |
| Vitamin mix (*1) | 1 |
| Choline bitartarate | 0.2 |

Note:
(*1) AIN (American Institute of Nutrition)
(*2) The amount corresponds to that for maintaining essential fatty acids of 1% by weight based on the total weight of the feed.
(*3) Vitamin-free, not less than 85% of crude protein

TABLE 4

Results of feeding

| Fat No. | FI (g/day) | WG (g/day) |
|---|---|---|
| I | 8.68 ± 0.67 | 1.21 ± 0.96 |
| II | 12.93 ± 1.13 | 4.53 ± 0.73 |
| III | 17.14 ± 0.93 | 6.78 ± 0.72 |
| IV | 20.48 ± 1.92 | 7.31 ± 1.06 |
| V | 17.32 ± 1.16 | 7.54 ± 2.06 |
| VI | 16.97 ± 0.26 | 7.38 ± 0.52 |
| VII | 17.01 ± 0.53 | 7.07 ± 1.08 |
| Control | 17.84 ± 0.52 | 8.87 ± 0.89 |

Experiment 1

The effects of Fats I to VII on the amount of ingestion of feed were compared by feeding rats.

SD male rats (5 weeks old, body weight: 120 to 140 g) was fed under the conditions of the temperature of 23° C.±1° C., the moisture of 55%±5% and the light-dark circle of 12 hours (illumination: 7:00 to 19:00). Firstly, preliminary feeding was conducted for one week by using commercially available solid feed ("Oriental CRF-1" manufactured by Oriental Yeast Kogyo K.K., Japan). Then, the rats were divided into groups (6 rats/group) and feeding was conducted for additional one week by freely supplying the rats with the feed of Table 3 (control: corn oil was substituted for Fats I to VII, i.e., feed containing 20 parts of corn oil).

Regarding each oil, the amount of ingestion (FI) and the body weight gain (WG) are shown in Table 4.

As is shown in Table 4, in comparison with the control, the amount of ingestion was decreased by 51% (Fat I) and 28% (Fat II) (both were significant with the risk rate P<0.001). At the same time, the body weight gain was extremely small in spite that the rats were in their growth period. Although the fatty acid composition and triglyceride composition of Fat III was similar to those of Fat I except that the bonding positions of caproic acid and stearic acid were different from each other, Fat III scarcely depressed ingestion. Since the fatty acid residue at the 2-position of Fats IV to VI were different from stearic acid residue, they also scarcely depressed ingestion.

Experiment 2

According to the same manner as that described in Experiment 1, preliminary feeding was conducted. Then, rats (6 rats/group) were fed with the feed having the same composition as shown in Table 3 containing Fat I or the control feed for 4 weeks, or fed with the feed having the same composition as shown in Table 3 containing Fat I for one week and then with the control feed for 3 weeks.

Figure 2:
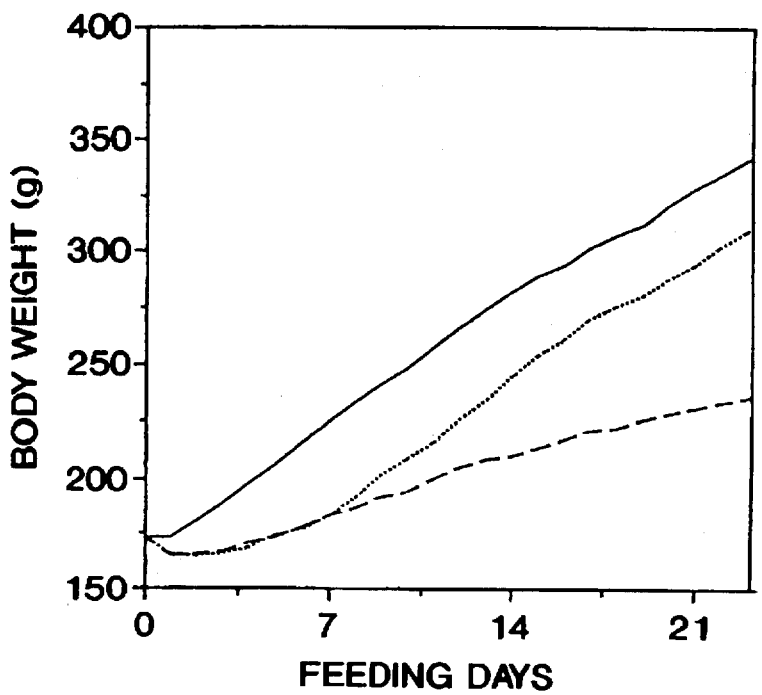
FIG. 2 is a graph showing the relation between the body weight and the number of feeding days obtained in Experiment 2 hereinafter.

The relation between the amount of ingestion of feed and feeding days as well as the relation between the body weight gain and feeding days are shown in FIGS. 1 and 2.

The amount of ingestion of the group wherein the feed containing Fat I was supplied (FIG. 1, the broken line) was significantly depressed for one week after initiation of the feeding. Then, although the depression effect was somewhat lowered, ingestion was depressed by about 70% in comparison with the group fed with the control feed containing only corn oil (FIG. 1, the solid line) and the depression was observed during the entire feeding period. In proportion to this, the body weight gain of the group fed with the feed containing Fat I (FIG. 2, the broken line) was significantly depressed in comparison with that of the group fed with the control feed containing only corn oil (FIG. 2, the solid line).

On the other hand, the amount of ingestion and the weight gain of the group wherein the feed containing Fat I was changed to the control feed one week after initiation of feeding (FIGS. 1 and 2, the dotted line) quickly recovered to the same levels as those of the group supplied with the control feed (FIGS. 1 and 2, the solid line).

This indicates that ingestion of the feed is depressed only during the period corresponding to feeding with the agent of the present invention, and that this effect of depression is a temporary action and is readily recovered. Thus, any sequela is scarcely expected.

Experiment 3

According to the same manner as described in Experiment 1, preliminary feeding was conducted. Then, rats were divided into three groups (6 rats/group). In the 1st group, rats were supplied with the feed containing Fat I as shown in Table 3. The rats of the 2nd group were supplied with the control feed containing only corn oil. The rats of the 3rd group were freely supplied both the feed containing Fat I as shown in Table 3 and the control feed. No substantial difference in the amounts of ingestion of the feed among these three groups until about 5 hours after initiation of feeding. However, after elapse of more than about 5 hours, difference in the amounts of ingestion was observed. Among these three groups, the amount of ingestion of the 2nd group (control feed) became the largest and the amount of ingestion of the 1st group (feed containing Fat I) became the smallest.

In the 3rd group (both control feed and feed containing Fat I), no substantial difference in the amounts of ingestion of the control feed and the feed containing Fat I until about 12 hours after initiation of feeding. However, after elapse of more than about 12 hours, the amount of ingestion of the control feed tended to become larger.

This indicates that Fat I per se does not have any taste or smell which is refused by the rats and that depression of ingestion of the present invention is not based on unpleasant taste, smell or mouthfeel.

EXAMPLE 3

Sugar (15.4 parts), salt (0.3 parts) and molten Fat I (20 parts) were admixed and to the mixture were added a chicken egg (10.3 parts), sodium bicarbonate (0.1 parts), ammonium bicarbonate (0.1 parts), low protein wheat flour (46.3 parts), skimmed milk powder (5.1 parts) and water (2.5 parts) to make a dough. The dough was baked at 170° to 180° C. for 10 to 15 minutes to produce hard cookie. Although the cookie thus obtained had no peculiar mouth feel and taste in comparison with the conventional hard cookie and was easily ingested. However, an appetite after ingestion was depressed for several hours.

EXAMPLE 4

To water (8 parts) was added skimmed milk powder (8 parts) and the mixture was uniformly dispersed by a homomixer and heated to 80° C. Then, to this mixture was added a Fat I (5 parts) containing lecithin (0.05 parts) with stirring. After conducting pre-emulsification, the mixture was homogenized under the pressure of 100 kg/cm$^3$, subjected to sterilization at 140° C. for 3 seconds and then quickly cooled to obtain an emulsified composition. The emulsified composition had milk-like taste and mouth feel and an appetite was depressed for several hours after drinking it.

EXAMPLE 5

To water (52 parts) were added casein sodium (5 parts) and skimmed milk powder (3 parts) and the mixture was uniformly dispersed by a homomixer and heated to 60° C. Then, to this mixture was added Fat I (40 parts) containing sucrose fatty acid ester (0.2 parts) with stirring. After conducting pre-emulsification, the mixture was homogenized under the pressure of 40 kg/cm$^2$ subjected to sterilization at 140° C. for 3 seconds and then, after cooling, aged at 5° C. for 24 hours to obtain an cream. The cream had no peculiar taste and mouth feel and an appetite was depressed for several hours after drinking it.

As described hereinabove, the agent of the present invention is useful for suppressing appetites and also useful for controlling overeating. Further, the agent can be easily substituted for other fats and oils without any disharmony, easily ingested in the form of oil-containing food or feed. Furthermore, the agent causes no patience and pain associated with alimentotherapy.

What is claimed is:

1. An appetite suppressing composition which comprises one or a plurality of triglycerides containing fatty acid residues having 2 to 10 carbon atoms at the 1,3-positions thereof and a stearic acid residue at the 2-position thereof which specified triglycerides are present in an amount of at least 50% by weight, based upon the entire triglycerides or fats and oils present.

2. An appetite suppressing composition according to claim 1, wherein the fatty acid residues bound at the 1,3-positions are straight chain saturated fatty acid residues having 2 to 8 carbon atoms.

3. An appetite suppressing composition according to claim 2, wherein the fatty acid residues bound at the 1,3-positions are straight chain saturated fatty acid residues having 6 to 8 carbon atoms.

4. A food containing an effective appetite suppressing amount of one or a plurality of triglycerides containing fatty acid residues having 2 to 10 carbon atoms at the 1,3-positions thereof and a stearic acid residue at the 2-position thereof which specified triglycerides are present in an amount of at least 50% by weight, based upon the entire triglycerides or fats and oils present.

5. A food according to claim 4, wherein the fatty acid residues bound at the 1,3-positions are straight chain saturated fatty acid residues having 2 to 8 carbon atoms.

6. A food according to claim 5, wherein the fatty acid residues bound at the 1,3-positions are straight chain saturated fatty acid residues having 6 to 8 carbon atoms.

7. Feed comprising an effective appetite suppressing amount of one or a plurality of triglycerides containing fatty acid residues having 2 to 10 carbon atoms at the 1,3-positions thereof and a stearic acid residue at the 2-position thereof which specified triglycerides are present in an amount of at least 50% by weight, based upon the entire triglycerides or fats and oils present.

8. Feed according to claim 7, wherein the fatty acid residues bound at the 1,3-positions are straight chain saturated fatty acid residues having 2 to 8 carbon atoms.

9. Feed according to claim 8, wherein the fatty acid residues bound at the 1,3-positions are straight chain saturated fatty acid residues having 6 to 8 carbon atoms.

10. A method of suppressing an appetite in an animal in need thereof, which comprises administering to the animal an effective appetite suppressing amount of a composition which comprises one or a plurality of triglycerides containing fatty acid residues having 2 to 10 carbon atoms at the 1,3-positions thereof and a stearic acid residue at the 2-position thereof which specified triglycerides are present in an amount of at least 50% by weight, based upon the entire triglycerides or fats and oils present.

* * * * *